US006779665B2

(12) United States Patent
Bolanos

(10) Patent No.: US 6,779,665 B2
(45) Date of Patent: Aug. 24, 2004

(54) GENEALOGY STORAGE KIT

(76) Inventor: Henry Bolanos, 34 Apt. D, Glenwood Ave., Norwalk, CT (US) 06854

( * ) Notice: Subject to any disclaimer, the term of this patent is extended or adjusted under 35 U.S.C. 154(b) by 7 days.

(21) Appl. No.: 10/223,808

(22) Filed: Aug. 20, 2002

(65) Prior Publication Data

US 2003/0042170 A1 Mar. 6, 2003

Related U.S. Application Data

(60) Provisional application No. 60/315,764, filed on Aug. 29, 2001.

(51) Int. Cl.[7] .............................................. B65D 69/00
(52) U.S. Cl. ...................... 206/569; 206/570; 206/459.5
(58) Field of Search ............................... 206/569, 223, 206/803, 570, 572, 435, 232, 459.5, 456, 363, 370

(56) References Cited

U.S. PATENT DOCUMENTS

| | | | | | |
|---|---|---|---|---|---|
| 4,106,597 | A | * | 8/1978 | Shook et al. ................ | 190/110 |
| 4,122,947 | A | * | 10/1978 | Falla ........................... | 206/569 |
| 4,303,610 | A | | 12/1981 | Sardisco et al. | |
| 4,657,138 | A | * | 4/1987 | Watson ....................... | 206/366 |
| 4,697,600 | A | * | 10/1987 | Cardenas et al. ........... | 128/753 |
| 4,964,509 | A | * | 10/1990 | Insley et al. ................ | 206/204 |
| 5,025,920 | A | * | 6/1991 | Walsh et al. ................ | 206/223 |
| 5,101,970 | A | | 4/1992 | Turner | |
| 5,131,404 | A | | 7/1992 | Neeley et al. | |
| 5,211,286 | A | * | 5/1993 | Turner ........................ | 206/223 |
| D336,849 | S | * | 6/1993 | Golias ......................... | D9/420 |
| 5,291,997 | A | * | 3/1994 | He et al. ..................... | 206/370 |
| D359,163 | S | * | 6/1995 | Summerfield et al. ....... | D3/205 |
| 6,036,019 | A | * | 3/2000 | Silverman ................... | 206/545 |
| 6,085,907 | A | * | 7/2000 | Hochmeister et al. ...... | 206/569 |
| 6,171,260 | B1 | * | 1/2001 | Hochmeister et al. ...... | 600/572 |
| 6,264,619 | B1 | * | 7/2001 | Ferguson .................... | 600/573 |
| 6,291,171 | B1 | | 9/2001 | Ricciardi et al. | |
| 6,427,834 | B1 | * | 8/2002 | Lin ........................ | 206/315.11 |
| 6,467,619 | B1 | * | 10/2002 | Leen et al. ................. | 206/421 |
| 6,579,271 | B1 | * | 6/2003 | Aruffo et al. ............... | 604/355 |

FOREIGN PATENT DOCUMENTS

| | | |
|---|---|---|
| DE | 196 02 299 A | 7/1997 |
| DE | 197 50 009 C | 9/1999 |
| GB | 2 206 410 A | 1/1989 |

OTHER PUBLICATIONS

"Evidence collection Jars" by Faurot.*
"Evidence Collection and Identification Kit" and "Faurot Customized Kits" by Faruot, see www.faurotinc.com.*
"Evident Crime Scene Products—Field Kits" by Evident Crime Scene Products, www.evidentcrimescene.com.*
"Evident Collection" by Evident Crime Scene Products, see www.evidentcrimescene.com.*
"Crime Scene Kit Cases" by Tri–Tech Inc., see www.tritechusa.com.*
European Search Report dated Dec. 4, 2002.

* cited by examiner

Primary Examiner—Shian T. Luong
(74) Attorney, Agent, or Firm—Scott D. Wofsy; Edwards & Angell, LLP

(57) ABSTRACT

A biological sample collection and storage kit s disclosed that includes a plurality of biological sample storage devices, a plurality of biological sample collection devices configured to collect biological samples for placement into the sample storage devices, identification devices for identifying the contents of the sample storage devices, and a housing including a base portion and a lid portion forming an interior cavity therebetween for accommodating the plurality of biological sample storage devices, the plurality of biological sample collection devices and the identification devices.

2 Claims, 4 Drawing Sheets

GENEALOGY STORAGE KIT

CROSS-REFERENCE TO RELATED APPLICATIONS

The subject application claims the benefit of priority from U.S. Provisional Patent Application Ser. No. 60/315,764 filed Aug. 29, 2001, the disclosures of which is herein incorporated by reference in its entirety.

BACKGROUND OF THE INVENTION

1. Field of the Invention

The subject invention is directed to a kit for collecting and maintaining biological material from an individual, such as material containing genetic information, as well as ancillary information about the individual.

2. Background of the Related Art

It is well known that genetic information is contained in a wide variety of biological tissues. DNA, the carrier of genetic information, is contained in nearly every cell of every living organism. This genetic information may be found in hair follicles, nails, teeth, skin cells, white blood cells, semen, and components of saliva. Urine, while not itself a carrier of genetic information, routinely includes components such as epithelial cells which contain ample genetic material for most purposes.

Genetic information collected from such biological samples may be utilized for a number of purposes. Among the many uses of genetic information collected from biological samples are identification of individuals; genetic testing and screening for hereditary conditions, diseases and disorders; and paternity and familial testing. In one illustrative use, parents may collect and safely store biological materials containing genetic information from their children. In the unfortunate event that a child subsequently goes missing, the parents can use the saved genetic material to aide in investigations concerning their missing child. Crime scene investigators can compare traces of biological materials left at a particular crime scene with the materials previously collected by the parents to help determine whether the child was previously at the crime scene in question.

As a further example, victims of rape may undergo physical examination after the crime has been committed in order to gather evidence. During this examination, reference samples of the victim's blood, saliva and/or hair may be collected, as well as any biological artifacts of the assailant which may be found on the victim's person. Genetic information of criminal assailants may be found in: saliva from bite marks; blood or skin cells from fingernail scrapings; semen or skin cells from inside or outside surface of condoms; semen, sweat, hair or saliva from blankets, pillow cases, sheets or other bed linens; hair, semen, blood or sweat from garments worn during or after an assault; and saliva from cigarette butts.

Genetic material may be collected from a variety of sources in a number of different manners. For example, living cells may scraped from soft tissue such as the basal mucosa (the lining of the mouth) using hard scrapers designed for such purposes. Alternatively, bodily fluids or cells may be collected using cotton swabs or similar devices, as disclosed, for example, in U.S. Pat. No. 6,291,171 to Ricciardi et al. which describes a kit for collection of basal mucosa cells utilizing cotton swabs. Additionally, bodily fluids may be collected using eyedroppers, pipettes or similar mechanisms designed for the uptake and dispensation of fluids. Similarly, fluids such as blood may be drawn directly from individuals by means of syringes generally utilized for such purpose. In many cases, it is normal practice to air dry specimens containing genetic material prior to storage.

Prior to acquisition of biological materials, it is important to ensure that the items to be used for sample collection and storage are free from contaminants such as biological materials originating from sources other than the intended source. Once cleaned of such foreign matter, the items must be maintained in such a manner so that they are not contaminated prior to their use. Individuals who are to collect and store the genetic material should be quickly able to ascertain whether the collection and storage articles have been maintained in a manner consistent with the goal of preventing contamination, or, conversely, if such protection against contamination has been compromised.

After being acquired, biological materials must be adequately stored until such time that analysis is to be undertaken. During storage, it is important that the collected samples be protected from contamination, degradation, and loss, among other detriments. To this end, it is desirable to store samples in sealable, protective containers. Suitable containers may include, among other types, sealable satchels such as zipper-sealable plastic or Tyvek brand bags, sealable paper or Glassine brand envelopes, and screw-cap enclosed glass or plastic vials. For example, U.S. Pat. No. 5,101,970 to Turner discloses a DNA collection kit which utilizes sealable plastic bags for storing collected materials.

During storage, it is important that samples be identifiable for such attributes as source, date of collection, location of collection and other pertinent information. To this end, one or more of a variety of labeling mechanisms may be employed, including markeable adhesive labels, string tags and markeable sleeves, among others. The labeling mechanisms should be capable of substantially permanent marking and should be resistant to alteration once marked.

In addition to genetic materials, individuals may wish to record and/or store ancillary information to augment genetic information. Such information may include dental records of individuals, which are often used to identify decomposed human remains; fingerprints, which are often used to identify individuals who had been present at crime scenes; and vital statistics such as name, eye color, hair color, birth date, height, weight, distinguishing marks, native language, mother's and father's names, guardian or next-of-kin contact information, blood type, medical conditions, necessary medications, and gender, among others. Photographs of individuals may also be stored to augment collected genetic information. When such information is collected and stored for children, it is advisable to update the information on a regular basis to ensure the information remains accurate as the child grows.

It is desirable, therefore, to provide a kit providing individuals with all the requirements for proper collection and storage of biological samples containing genetic information. It is also desirable to include in the aforementioned kit additional means to record and store ancillary information with which to augment the biological samples containing genetic information.

SUMMARY OF THE INVENTION

The subject invention is directed to a new and useful genealogy storage kit and more particularly to a biological sample collection and storage kit. The kit includes a plurality of biological sample storage devices, a plurality of biological sample collection devices configured to collect biological samples for placement into the biological sample storage devices, a plurality of biological sample identification devices for identifying the contents of the sample storage devices. The kit further includes a housing having a base portion and a lid portion hinged together to form an interior cavity for accommodating the plurality of biological sample storage devices, the plurality of biological sample collection devices and the plurality of biological sample identification devices.

In one embodiment of the invention, a preformed insert is disposed within the base portion of the housing which has a plurality of recesses dimensioned and configured to retain the plurality of biological sample storage devices. In another embodiment, the housing includes a latch for maintaining the lid portion and the base portion in a closed position.

Preferably, the plurality of biological sample storage devices include closable storage vials, and more particularly, a plurality of glass storage vials and plastic storage vials of varying capacity. Other types of sample storage devices may also be included, such as sealable bags, pouches and the like. The plurality of biological sample collection devices are selected from the group consisting of scrapers, swabs, syringes and pipettes. Other type of sample collection devices may also be included, such as tweezers or the like. The plurality sample identification devices are selected from the group consisting of adhesive labels, string tags, markeable sleeves. Other type of sample identification devices may also be included.

In an embodiment of the invention, the kit further includes means for recording ancillary information about an individual, including, for example, means for recording the fingerprints of an individual, and a data recordation card for recording vital statistics of an individual. Preferably, the kit includes a storage sleeve for maintaining the means for recording ancillary information. The storage sleeve is affixed to an interior surface of the lid portion of the housing, or in another readily accesible location within the housing.

These and other aspects of the subject invention will become more readily apparent to those having ordinary skill in the art from the following description of the invention taken in conjunction with th drawings described hereinbelow.

BRIEF DESCRIPTION OF THE DRAWINGS

So that those having ordinary skill in the art to which the subject invention pertains will more readily understand how to make and use the subject invention, preferred embodiments of the invention be described in detail hereinbelow with reference to the drawings, wherein.

DETAILED DESCRIPTION OF THE PREFERRED EMBODIMENTS

Figure 1:
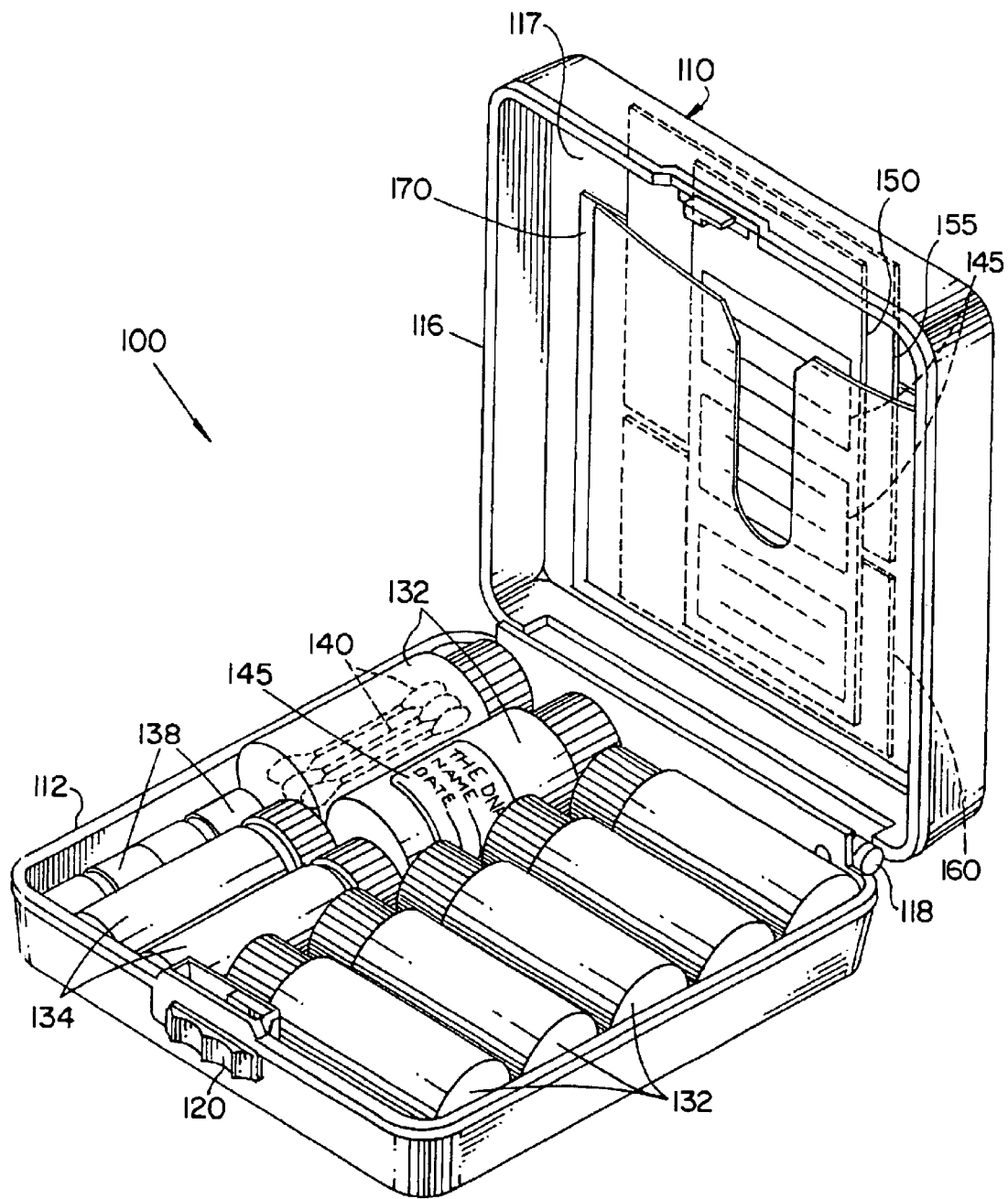
FIG. 1 is a perspective view of a genealogy storage kit constructed in accordance with a preferred embodiment of the subject invention.
Figure 2:
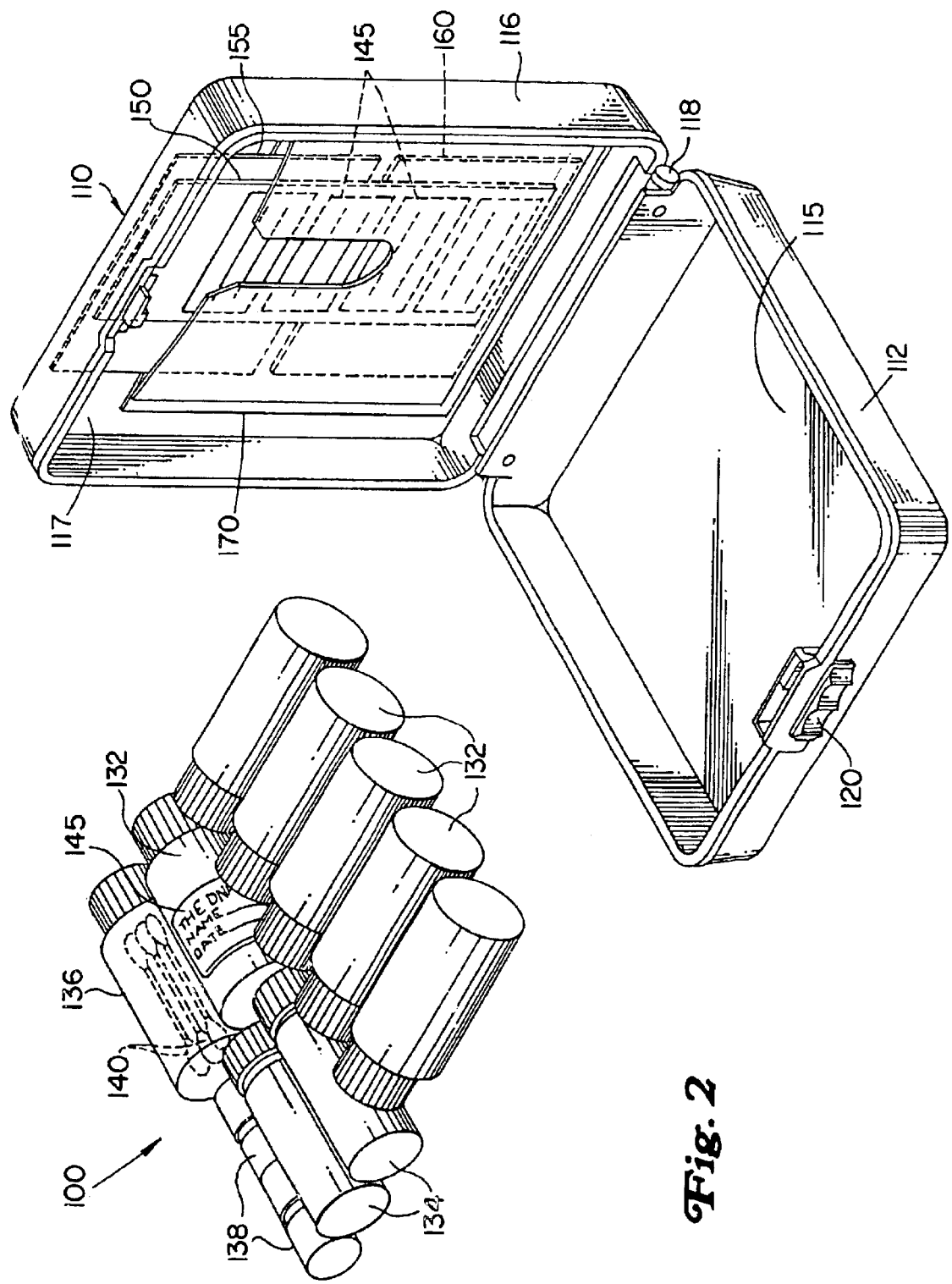
FIG. 2 is an exploded perspective view of the genealogy storage kit of FIG. 1 illustrating the interior of the kit housing which houses, among other things, sample storage devices, sample collection devices and sample identification devices.

Referring now to the drawings wherein like reference numerals identify similar structural features of the several embodiments of the subject invention, there is illustrated in FIGS. 1 and 2 a genealogy storage kit constructed in accordance with a preferred embodiment of the subject invention and designated generally by reference numeral 100. Genealogy storage kit 100 includes a housing 110 formed from a light weight, high strength structural material. The housing 110 includes a base portion 112 having plural upstanding side walls extending from a floor 115, and a lid portion 116 having plural side walls projecting from ceiling 117.

Together, the base portion 112 and lid portion 116 form an interior cavity within the housing 110. The base portion 112 and lid portion 116 are connected by a hinge 118 such that lid portion 116 may open and close relative to base portion 112. A latch mechanism 120 is associated with the base portion 112 and lid portion 116 for maintaining the lid portion 116 in a closed position. The housing 110 is adapted and configured to accommodate low temperature storage, if desired.

With continuing reference to FIGS. 1 and 2, the housing 110 of storage kit 100 contains a plurality of sample storage devices in the form of sealable vials of varying size and capacity, including, for example, large plastic storage vials 132, medium plastic storage vials 134, and small glass storage vials 136, each with a threaded cap or similar closure. The storage vials are adapted to safely maintain hair follicles, nails, teeth, saliva and other biological material collected from an individual. The storage vials are suitable for low temperature storage.

The housing 110 of storage kit 100 further contains a plurality of sample collection devices for collecting biological material from an individual for placement into the storage devices. As illustrated, collection devices include a plurality of cotton swabs 140 contained within plastic storage vial 132. Other devices, while not shown, may be provided in storage kit 100 including, for example, scrapers, syringes and pipettes for collecting various types of biological sample materials. The housing 110 of storage kit 100 further contains sample identification devices. Preferably, the sample identification devices are in the form of adhesive labels 145, one of which is shown affixed to a sealable storage vial 132, the remainder of which are provided on a sheet 150 disposed in the kit housing 110. Different sized labels may be provided for the different sized vials, and other sample identification devices may be utilized so long as they facilitate recordation of a sufficient amount of information to identify the contents of a vial.

The storage kit 100 of the subject invention further includes devices to store ancillary information about the individual from whom the biological sample materials have been collected and stored in the kit. These include a fingerprint recordation device 155 which has ink or a similar media for making an imprint of an individual's fingerprints, and a data recordation card 160 specifically designed for recording vital statistics about the individual, such as eye color, hair color, birth date, height, weight, distinguishing marks, blood type, medical conditions, etc. A flexible sleeve or pocket 170 is affixed to an interior surface of the lid portion 116 of housing 110 for securely maintaining fingerprint recordation device 150 and data recordation card 160. The sample identification devices may also be maintained within sleeve 170 for ready access by an individual, as well as photographs of the individual.

Figure 3:
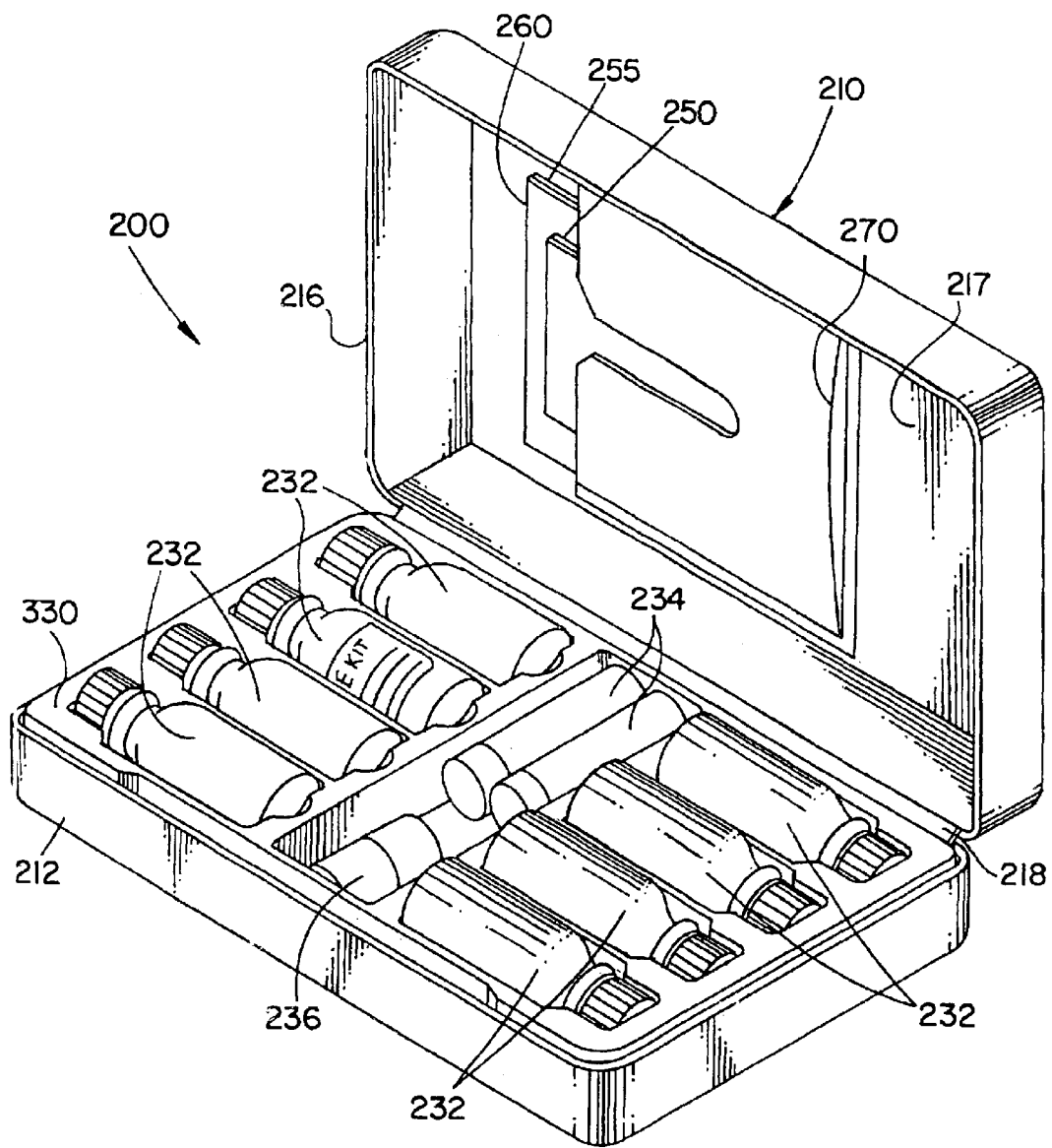
FIG. 3 is a perspective view of another genealogy storage kit constructed in accordance with a preferred embodiment of the subject invention.
Figure 4:
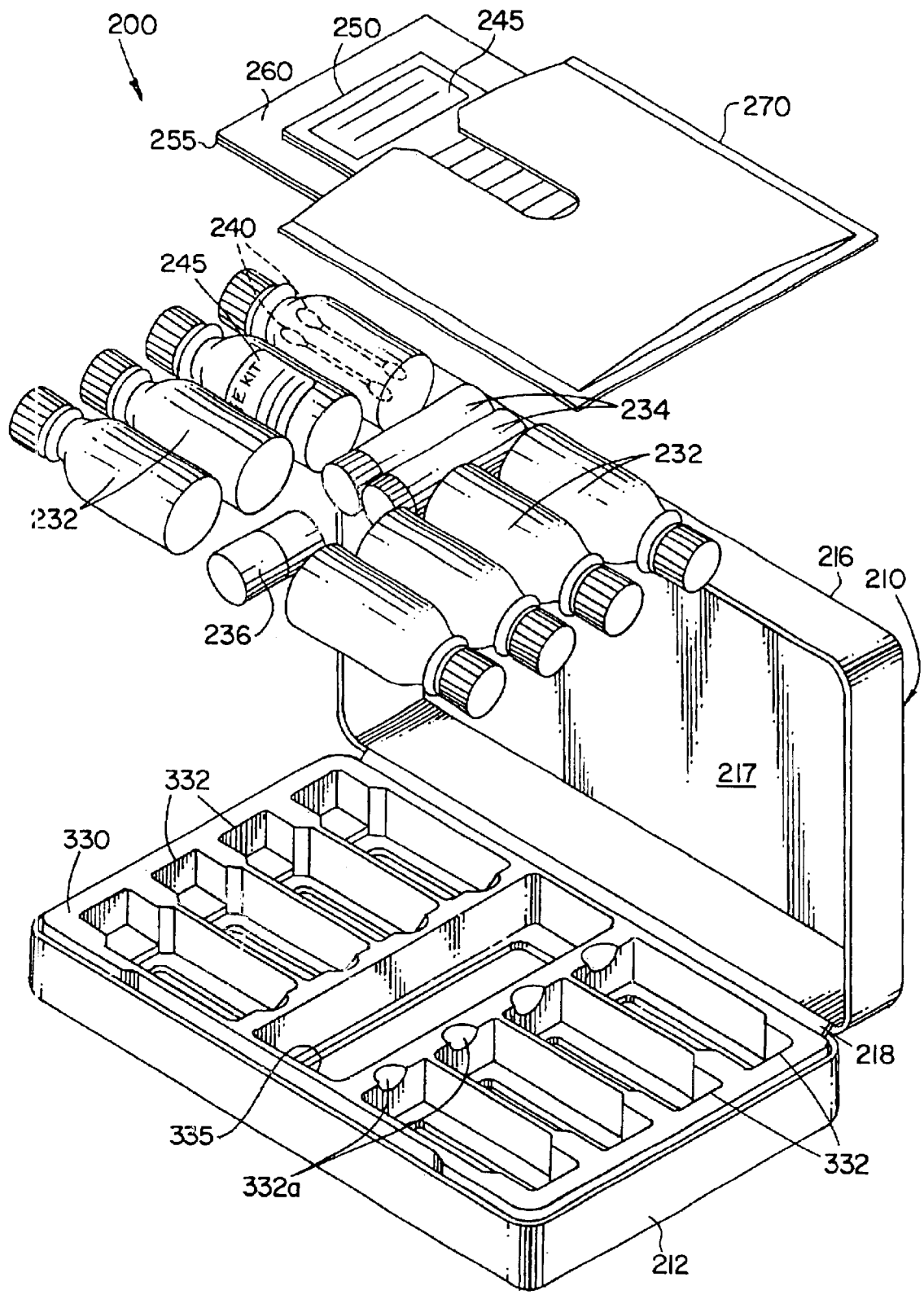
FIG. 4 is an exploded perspective view of the genealogy storage kit of FIG. 3 illustrating the interior of the kit housing which houses, among other things, a preformed insert for accommodating a plurality of sample storage devices.

Referring now to FIGS. 3 and 4, there is illustrated another genealogy storage kit constructed in accordance with a preferred embodiment of the subject invention and designated generally by reference numeral 200. Storage kit 200 includes a generally rectangular housing 210 formed by a base portion 212 and a lid portion 216 constructed of a light weight, rigid material and connected to one another along hinge 218. The kit 200 and its contents are designed for low temperature storage, if desired by the collector.

Storage kit 200 is substantially similar to storage kit 100 in that it includes glass and/or plastic closable storage vials 232, 234 and 236 of varying size, as well as sample collection devices such as cotton swabs 240, sample identification devices such as the sheet 250 of adhesive labels 245. Storage kit 200 also includes ancillary information recordation devices such as a fingerprint recordation device 255 and a data recordation card 260 for recording vital statistics about the individual. These devices are maintained in a sleeve 270 which may be affixed to the lid portion 216 or simply disposed within the interior of the housing 210.

Genealogy storage kit 200 differs however from storage kit 100 in that it has a preformed plastic insert 330 disposed within the base portion 212 of kit housing 200. The preformed insert 330 is preferably removable from the base portion 212 and has a plurality of recesses dimensioned and configured to retain the plurality of closable storage vials. These includes a two rows of vial shaped recesses 332 for accommodating the large glass storage vials 232, and a central recess 335 formed between the two rows for accommodating several of the smaller glass storage vials 234 and 236. Each vial shaped recess 332 of insert 330 has a depression 332a formed therein at the forward end of the recess for gaining ready access to the vial disposed therein.

In both embodiments of the subject invention, the housing of the storage kit will have provisions for imprinting thereon of otherwise attaching thereto the name, identification or emblem of a sponsor, such as, for example, a company, union or governmental agency. This will enable the kit to be marketed to select groups for distribution to its members. In addition, the housing will have provisions for imprinting thereon or otherwise attaching thereto the name and address of the owner and collector of the kit.

Although the genealogy storage kit of the subject invention has been described with respect to certain preferred embodiments, those skilled in the art will readily appreciate that changes and modifications may be made thereto without departing from the spirit and scope of the present invention as defined by the appended claims.

What is claimed is:

1. A biological sample collection and storage kit adapted for low temperature storage comprising:

a) a plurality of storage vials of varying capacity suitable for low temperature storage, wherein each of the storage vials has a threaded cap and is adapted to store a different biological sample collected from an individual;

b) a plurality of collection devices configured to collect biological samples from an individual for placement into the plurality of storage vials, wherein collection devices are contained within one of the plurality of storage vials for ready removal and subsequent use;

c) a plurality of adhesive labels for identifying the biological samples stored within each of the plurality of storage vials;

d) a housing including a base portion and a lid portion joined together along a horizontal hinge to form an interior cavity therebetween for accommodating the plurality of storage vials in a horizontal orientation, wherein the housing is adapted and configured to accommodate low temperature storage;

e) a removable preformed insert disposed within the base portion of the housing, the removable preformed insert having a plurality of recesses formed therein, wherein each of the recesses is dimensioned and configured to accommodate a storage vial in a horizontal orientation relative to the horizontal hinge of the housing; and f) a storage sleeve affixed to an interior surface of the lid portion, wherein the storage sleeve contains, the plurality of adhesive labels, means for recording fingerprints and a data recordation card for recording vital statistics of an individual from whom biological samples have been collected and stored within the kit.

2. A biological sample collection and storage kit adapted for low temperature storage comprising:

a) a plurality of relatively large glass storage vials and a plurality of relatively small glass storage vials, wherein each of the glass storage vials has a threaded cap and is adapted to store a different biological sample collected from an individual;

b) a plurality of collection devices configured to collect biological samples from an individual for placement into the plurality of glass storage vials, wherein collection devices are contained within one of the relatively large glass storage vials for ready removal and subsequent use;

c) a housing including a base portion and a lid portion joined together along a horizontal hinge to form an interior cavity therebetween for accommodating the plurality of glass storage vials in a horizontal orientation;

d) a removable preformed insert disposed within the base portion of the housing, the removable preformed insert having two parallel rows of recesses formed therein for accommodating the plurality of relatively large glass storage vials, and a central recess formed between the two parallel rows of recesses for accommodating the plurality of relatively small glass storage vials; and e) a storage sleeve affixed to an interior surface of the lid portion, wherein the storage sleeve contains a sheet carrying a plurality of adhesive labels for identifying the biological samples stored within each of the plurality of glass storage vials, means for recording fingerprints and a data recordation card for recording vital statistics of an individual from whom biological samples have been collected and stored within the kit.

* * * * *